(12) United States Patent
Bonnette et al.

(10) Patent No.: US 9,108,019 B2
(45) Date of Patent: Aug. 18, 2015

(54) CATHETER SYSTEM

(71) Applicant: Boston Scientific Limited, Hamilton HM11 (BM)

(72) Inventors: Michael J. Bonnette, Minneapolis, MN (US); Leif E. Leirfallom, Plymouth, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 35 days.

(21) Appl. No.: 13/801,581

(22) Filed: Mar. 13, 2013

(65) Prior Publication Data
US 2014/0276602 A1 Sep. 18, 2014

(51) Int. Cl.
*A61M 25/00* (2006.01)
*A61M 25/01* (2006.01)
*A61M 5/142* (2006.01)
*A61M 5/00* (2006.01)
*A61B 17/22* (2006.01)

(52) U.S. Cl.
CPC ............ *A61M 25/007* (2013.01); *A61M 5/007* (2013.01); *A61M 5/142* (2013.01); *A61M 25/01* (2013.01); *A61B 2017/22084* (2013.01); *A61M 25/0105* (2013.01); *A61M 2025/0004* (2013.01); *A61M 2025/006* (2013.01); *A61M 2025/0008* (2013.01); *A61M 2025/0175* (2013.01)

(58) Field of Classification Search
CPC .................. A61M 25/007; A61M 2025/0004; A61M 25/0071; A61M 25/01; A61M 25/0105; A61M 5/48; A61M 1/0028; A61M 2025/0008
USPC .......................................... 604/246, 264, 523
See application file for complete search history.

(56) References Cited

U.S. PATENT DOCUMENTS

| | | | |
|---|---|---|---|
| 3,698,195 A * | 10/1972 | Chapin | 405/44 |
| 5,324,259 A | 6/1994 | Taylor et al. | |
| 5,425,723 A * | 6/1995 | Wang | 604/523 |
| 6,520,930 B2 | 2/2003 | Critchlow et al. | |
| 6,575,932 B1 * | 6/2003 | O'Brien et al. | 604/101.01 |
| 6,676,637 B1 | 1/2004 | Bonnette et al. | |
| 6,945,951 B1 | 9/2005 | Bonnette et al. | |
| 7,641,645 B2 | 1/2010 | Schur | |
| 7,666,169 B2 | 2/2010 | Cowan et al. | |
| 7,935,092 B1 | 5/2011 | Odland et al. | |
| 8,932,270 B2 * | 1/2015 | O'Day | 604/256 |
| 2005/0197633 A1 | 9/2005 | Schwartz et al. | |
| 2006/0129091 A1 | 6/2006 | Bonnette et al. | |
| 2008/0275393 A1 * | 11/2008 | Bonnette et al. | 604/102.01 |
| 2011/0257622 A1 * | 10/2011 | Salahieh et al. | 604/500 |

OTHER PUBLICATIONS

International Search Report and Written Opinion mailed on Jun. 2, 2014 from corresponding PCT Application No. PCT/US2014/020336 filed on Mar. 4, 2014.

* cited by examiner

*Primary Examiner* — Quynh-Nhu H Vu
(74) *Attorney, Agent, or Firm* — Seager, Tufte & Wickhem, LLC (57) ABSTRACT

A multi-station hydrodynamic catheter includes an outer catheter having a first lumen, the outer catheter having a plurality of orifice stations positioned along a portion of the outer catheter, where each orifice station includes one or more orifices extending from an outer catheter external surface to the first lumen. The multi-station hydrodynamic catheter includes an inner catheter having a second lumen, the inner catheter movable within the first lumen and includes at least one emanator, where the at least one emanator includes one or more fluid delivery ports extending from an inner catheter external surface to the second lumen.

10 Claims, 6 Drawing Sheets

FIG. 8 ized fluid delivery along multiple orifice stations, a catheter system is provided that quickly and effectively treats the blood clot. The pressurized fluid delivery facilitates the fluid to initially interact with a portion of the blood clot adjacent to a blood vessel upon introduction of the fluid jet. Since the fluid comes into contact with the portion of the blood clot adjacent to the blood vessel wall initially, the amount of time for the fluid to interact with the blood clot is reduced, thereby enhancing the efficiency of the thrombectomy technique.

CATHETER SYSTEM

TECHNICAL FIELD

This document pertains generally, but not by way of limitation, to a catheter system configured to remove blockage within a patient's vessel.

BACKGROUND

A thrombectomy is a medical procedure used to remove a blood clot (e.g., thrombus) from a vessel, such as an artery or vein. If a thrombus is not removed, it may obstruct blood flow. In one technique, the thrombus can be removed by a thrombectomy procedure such as thrombolysis which is the breakdown of a thrombus by pharmacological means. Thrombolysis can introduce thrombolytic drugs to the site of the blood clot. The thrombolytic drugs can interact with the thrombus and actively reduce the size (e.g., breakdown, dislodge, minimize, or eliminate) the thrombus.

OVERVIEW

The present inventors have recognized, among other things, that a problem to be solved includes decreasing a thrombectomy procedure time without sacrificing the effectiveness of the procedure. For example, existing systems and methods for performing a thrombectomy procedure can include weeping thrombolytic drugs to the site of a blood clot over many hours or days (e.g., overnight to about three days). Weeping can include exuding a thrombolytic drug into the blood vessel at the blood clot site at low pressure (e.g., below 4 pounds per square inch (psi)). Weeping the thrombolytic drugs into the blood vessel does not provide deep penetration into the blood clot and can increase the time for the thrombolytic drugs to interact with the portion of the blood clot adjacent to a blood vessel wall. That is, the thrombolytic drugs introduced via weeping may interact with a surface of the blood clot initially, and over time may come into contact with the portion of the blood clot adjacent to the blood vessel wall.

The present subject matter provides a solution to this problem, by providing a catheter system and method that quickly and effectively treats a blood clot. The present subject matter reduces the procedure time and enhances the effectiveness of thrombectomy.

In an example, the present subject matter provides a catheter system comprising a multi-station hydrodynamic catheter. The multi-station hydrodynamic catheter includes an outer catheter having a first lumen and a plurality of orifice stations positioned along a portion of the outer catheter and an inner catheter having a second lumen. The inner catheter includes at least one emanator and is movable within the first lumen. In an example, the inner catheter moves within the first lumen between a first orifice station and a second orifice station of the plurality of orifice stations. When the inner catheter is positioned at the first orifice station, fluid delivery ports of the emanator are in fluid communication with one or more orifices of the first orifice station. When the inner catheter is positioned at the second orifice station, fluid delivery ports of the emanator are in fluid communication with one or more orifices of the second orifice station.

The catheter system of the present disclosure provides treating a blood clot along multiple stations (e.g., the plurality of orifice stations). For example, at the first orifice station a first fluid jet is pumped into the vessel and then advanced to the second orifice station where a second fluid jet is pumped into the vessel. That is, the blood clot is treated in multiple steps along the length of the clot, where at each step (e.g., an orifice station) a fluid jet is pumped into the vessel. By providing the direct pressurized delivery along multiple orifice stations, the fluid penetrates the blood clot more effectively and reduces the procedure time as compared to other methods. For example, the direct pressurized delivery facilitates the fluid to initially interact with a portion of the blood clot adjacent to a blood vessel upon introduction of the fluid jet. Since the fluid comes into contact with the portion of the blood clot adjacent to the blood vessel wall initially, the amount of time for the fluid to interact with the blood clot is reduced, thereby enhancing the efficiency of the thrombectomy technique. Thus, the present subject matter reduces the procedure time and enhances the effectiveness of thrombectomy.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
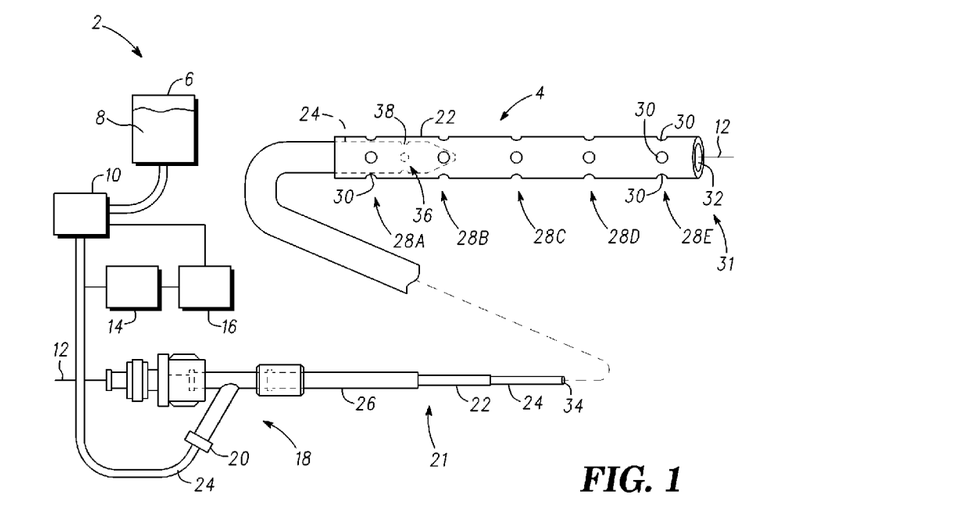
FIG. 1 illustrates a catheter system, in accordance with one embodiment of the present disclosure.

FIG. 1 illustrates a catheter system 2, in accordance with one embodiment of the present disclosure. As will be described in detail herein, the catheter system 2 is configured to provide a pressurized fluid (e.g., thrombolytic drugs) at multiple stations for removal or breakdown of thrombus from a vessel such as an artery or vein. By providing direct pressurized fluid delivery along the multiple stations, the pressurized fluid penetrates the blood clot more effectively and reduces the procedure time as compared to other methods. In one example, the thrombolytic drugs delivered to the vessel include, but are not limited to, lytics (e.g., tissue plasminogen activator (tPA)) or other drugs that interact with the thrombus and actively reduce the size (e.g., breakdown, dislodge, minimize or eliminate) the thrombus. In some examples, after the catheter system 2 delivers the lytics or other drugs to actively reduce the size of the thrombus, a thrombectomy catheter is used to further macerate and aspirate any remaining thrombus within the vessel. For example, once catheter system 2 has treated the thrombus with the lytics or other drugs, the thrombectomy catheter is used to clear any remaining thrombus. In an example, using the catheter system 2 in combination with a thrombectomy catheter can reduce the overall procedure time. Examples of thrombectomy catheters are described in Bonnette et al., U.S. Patent Publication No. 2006/0129091, entitled "ENHANCED CROSS STREAM MECHANICAL THROMBECTOMY CATHETER WITH BACKLOADING MANIFOLD," Bonnette et al., U.S. Pat. No. 6,676,637, entitled "SINGLE OPERATOR EXCHANGE FLUID JET THROMBECTOMY METHOD," and Bonnette et al., U.S. Pat. No. 6,945,951, entitled "THROMBECTOMY CATHETER AND SYSTEM," which are hereby incorporated herein by reference in their entirety.

In an example, the catheter system 2 includes a multi-station hydrodynamic catheter 4 in association with a manifold assembly 18. The hydrodynamic catheter 4 includes an outer catheter 22 and an inner catheter 24, where the inner catheter 24 is moveable within the outer catheter 22. In an example, the outer catheter 22 is coupled to and extends distally from the manifold assembly 18. The outer catheter 22 includes a first lumen 32 that extends along a length of the outer catheter 22 (e.g., from a proximal end 21 to a distal end 31) In an example, the outer catheter 22 includes a plurality of orifice stations 28A-E (collectively referred to as "orifice stations 28") positioned along a portion of the outer catheter 22. In an example, the portion of the outer catheter 22 that includes the plurality of orifice stations 28 is a distal portion of the outer catheter 22. Each orifice station 28 of the plurality of orifice stations 28 includes one or more orifices 30 configured to deliver the pressurized fluid to a vessel.

Figure 2:
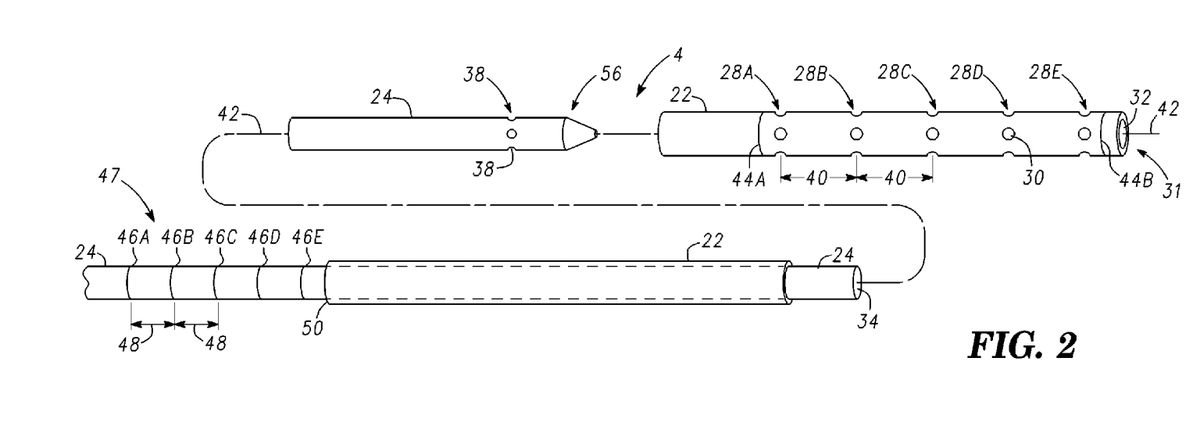
FIG. 2 illustrates an exploded view of a multi-station hydrodynamic catheter, in accordance with one embodiment of the present disclosure.

In an example, the inner catheter 24 includes a second lumen 34 extending along a length of the inner catheter 24. The inner catheter 24 is positioned within the first lumen 32 of the outer catheter 22. The inner catheter 24 includes at least one emanator 36 including one or more fluid delivery ports 38. As discussed herein, the inner catheter 24 is movable within the outer catheter 22 such that, at multiple positions within the outer catheter 22, the emanator 36 aligns with each one of the plurality of orifice stations 28. For example, when the emanator 36 is aligned with a first orifice station 28A of the plurality of orifice stations 28, the one or more fluid delivery ports 38 of the emanator 36 are in fluid communication with the one or more orifices 30 of the first orifice station 28A. As shown in FIG. 2, the second lumen 34 is configured to deliver the pressurized fluid to the one or more fluid delivery ports 28 and to the one or more respective orifices 30 of the first orifice station 28A used in a thrombectomy procedure. In an example, the pressurized fluid within the lumen 34 has pressures including, but not limited to, about 5 psi to about 100 psi. In an example, the one or more orifices 30 provide corresponding fluid jets at flow rates including, but not limited to, about 1 meter per second (m/s) to about 30 m/s (or a shear rate low enough to not cause appreciable hemolysis).

In operation, the hydrodynamic catheter 4 is inserted into a vessel, such as a vein or artery, and pressurized fluid is delivered to the emanator 36 via the second lumen 34 and subsequently to a first orifice station 28A of the plurality of orifice stations 28. The fluid is delivered through one or more orifices 30 of the first orifice station 28A, and is hydrodynamically delivered into the thrombus within the vessel (e.g., by way of fluid pressure, fluid velocity, and fluid flow volume). For instance, the pressurized fluid (e.g., a thrombolytic fluid) impacts and penetrates the thrombus local to the first orifice station 28A and actively reduces the size (e.g., breaks down) and minimizes or eliminates the thrombus.

As discussed below, after a volume of the fluid is delivered to the vessel via the one or more orifices 30 of the first orifice station 28, the inner catheter 24 is advanced within the outer catheter 22 such that the emanator 36 is aligned with a second orifice station 28B of the plurality of orifice stations 28. When aligned with the second orifice station 28B, a volume of the fluid is delivered to the vessel via the one or more orifices 30 of the second orifice station 28B. The inner catheter 24 is advanced within the outer catheter 22 such that the volume of fluid is delivered to the vessel at each orifice station 28A-E of the plurality of orifice stations 28. As is shown in FIG. 2, the second orifice station 28B (and the distal orifice stations 28B-28E) are axially spaced from the first orifice station 28A. Accordingly, the fluid is delivered at a localized point by way of each of the orifice stations 28A-E to differing locations within a vessel (or along a large thrombus deposit).

In an example, the manifold assembly 18 can have multiple structures extending therefrom or attached thereto including, but not limited to, the hydrodynamic catheter 4. As shown in FIG. 1, a strain relief fitting 26 is coupled between the hydrodynamic catheter 4 and the manifold assembly 18. In an example, a proximal end 21 of the outer catheter 22 is secured to the manifold assembly 18. The inner catheter 24 extends through and is moveable within a side port 20. A fluid delivery device 10 can be coupled to the inner catheter 24 and the side port 20 to deliver a pressurized fluid to the fluid delivery ports 38 of the emanator 36. The fluid delivery device 10 (e.g., a pump or injector) pumps a volume of a fluid 8 from a fluid reservoir 6 into the second lumen 34 to generate a pressurized source of fluid within the second lumen 34. In an example, the fluid 8 includes thrombolytic drugs such as lytics, and the pressurized source of fluid generates fluid jets when directed through the one or more orifices 30 of each of the orifice stations 28A-E. In an example, a contrast injector is used as the fluid delivery device 10. The contrast injector can inject a contrast media into the patient. In an example, the contrast injector is used in the beginning of the procedure to understand where the clot is and the clots magnitude and at the end of the procedure to verify the thrombus has been sufficiently removed. Examples of the fluid delivery device 10 are described in Cowan et al., U.S. Pat. No. 7,666,169, entitled "SYRINGE AND SYRINGE PLUNGERS FOR USE WITH MEDICAL INJECTORS" and Critchlow et al., U.S. Pat. No. 6,520,930, entitled "INJECTORS, INJECTOR SYSTEMS AND INJECTOR CONTROL", which are hereby incorporated herein by reference in their entirety.

Referring again to FIG. 1, a motor 14 is optionally coupled to the inner catheter 24. The motor 14 advances (e.g., moves) the inner catheter 24 within the outer catheter 22 between the plurality of orifice stations 28. A control unit 16 is operably coupled with the fluid delivery device 10 and the motor 14. In an example, the control unit 16 provides one or more of monitoring and control of the motor 14 and corresponding movement of the inner catheter 24 within the outer catheter 22. For example, the control unit 16 operates the motor 14 to selectively move the inner catheter 24 from, for example, a first orifice station 28A to a second orifice station 28B. Additionally, the control unit 16 operates the fluid delivery device 10 to selectively deliver a volume of the fluid 8 (e.g., a predetermined volume of fluid) over a period of time (e.g., a predetermined period of time), when the multi-station hydrodynamic catheter 4 is at each one of the plurality of orifice stations 28.

FIG. 2 illustrates an exploded view of a multi-station hydrodynamic catheter 4, in accordance with one embodiment of the present disclosure. In an example, the outer catheter 22 includes the plurality of orifice stations 28 positioned along a portion of the outer catheter 22. As illustrated in FIG. 2, the outer catheter 22 includes five orifice stations 28A-E. Optionally, more or less than five orifice stations 28 are incorporated into the outer catheter 22 in other examples. The plurality of orifice stations 28 are symmetrically spaced along a longitudinal axis 42 of the outer catheter 22. In an example, each orifice station 28 is spaced from an adjacent orifice station 28 by a distance 40. In one example, the distance 40 between each of the orifice stations 28 is equal. In another example, the distance 40 between each orifice station 28 varies along the length of the outer catheter 22. In an example, the number and spacing of the orifice stations 28 vary based on one or more of the location and size of the thrombus to be removed, the vascular location of the thrombus or the like.

As illustrated in FIG. 2, the plurality of orifice stations 28 each include one or more orifices 30. In an example, each orifice station 28 includes four orifices 30 that are radially spaced along a periphery of the outer catheter 22 (e.g., symmetrically spaced around the outer catheter periphery). In an example, the orifice stations 28 include more or less than four orifices 30. In another example, the number of orifices 30 at each orifice station 28 can vary between the plurality of orifice stations 28. As illustrated in FIG. 2, the orifices 30 at each orifice station 28 are generally located on a plane that is perpendicular to the longitudinal axis 42 of the outer catheter 22. In still another example, the orifices 30 of an orifice station 28 are staggered such that the one or more orifices 30 of a particular orifice station 28 are arranged in a non-planar fashion that is substantially perpendicular to the longitudinal axis 42.

As illustrated in FIG. 2, the one or more orifices 30 have a circular shape. In an example, the one or more orifices 30 can have a number of different shapes. For example, the one or more orifices 30 include, but are not limited to, circular, ovular, square, triangular, trapezoidal, polygonal, parallelogram, rhomboidal, and other irregular shapes.

In another example, the outer catheter 22 includes a radiopaque markers 44A-B (collectively "radiopaque markers 44") that are visible when viewed by an imaging device, such as an X-ray machine, a magnetic resonance imaging (MRI) device, a computed tomography (CT) scan, a computed axial tomography (CAT) scan, a positron emission tomography (PET) scan, an ultrasound device or the like. In an example, the radiopaque markers 44 are positioned on each side of the plurality of orifice stations 28. For example, a first radiopaque marker 44A is positioned proximal to a first orifice station 28A, a second radiopaque marker 44B is positioned distal to a last orifice station 28E. The radiopaque markers 44 provide guidance regarding the positioning of the outer catheter 22 within a vessel. For example, the radiopaque markers 44 facilitate the positioning of the plurality of orifice stations 28 along a portion of the vessel including the thrombus.

The inner catheter 24 shown in FIG. 2 includes at least one emanator 36 having one or more fluid delivery portions 38. The at least one emanator 36 is positioned toward a distal portion 56 of the inner catheter 24. As illustrated in FIG. 2, the inner catheter 24 includes a single emanator 36. In other examples more than one emanator 24 is positioned along the inner catheter 24. Where more than one emanator 24 is used, a distance between each one of the emanators 36 optionally equals the distance 40 between each of the plurality of orifice stations 28.

In the configuration shown in FIG. 2, the one or more fluid delivery ports 38 have a similar configuration to the one or more orifices 30 such that, when the emanator 36 is aligned with one of the plurality of orifice stations 28, the fluid delivery ports 38 are aligned and in fluid communication with the one or more orifices 30 to deliver the fluid to the vessel. For example, similar to the orifices 30 of the plurality of orifice stations 28, the one or more fluid delivery ports 38 are radially spaced along a periphery of the inner catheter 24. In an example, the number of fluid delivery ports 38 of the emanator 36 equals the number of orifices 30 of each of the orifice stations 28. In an example, the one or more orifices 30 have a variety of different shapes. For example, the one or more fluid delivery ports 38 have a circular, ovular, square, triangular, trapezoidal, polygonal, parallelogram, rhomboidal, or other irregular shape. In an example, the shape and size of the fluid delivery ports 38 of the emanator 36 are substantially the same as the shape and size of the one or more orifices 30 of the orifice stations 28. In another example, the shape and size of the fluid delivery ports 38 are different from the shape and size of the one or more orifices 30.

Optionally, the inner catheter 24 includes a plurality of station reference markers 46A-E (collectively referred to as "station reference markers 46") positioned along a proximal portion 47 of the inner catheter 24. In the example shown, the number of the station reference markers 46 is equal to the number of orifice stations 28 positioned along the outer catheter 22. The station reference markers 46 are spaced apart a distance 48 that is substantially the same as the distance 40 between the plurality of orifice stations 28. The station reference markers 46 aide an operator to advance the inner catheter 24 from a first orifice station (e.g., orifice station 28A) to a second orifice station (e.g., orifice station 28B) and any other distal orifice station 28. In an example, when the most-distal station reference marker 46E abuts a reference portion 50 of the outer catheter 22, the emanator 36 is aligned with a first orifice station 28A. When the most-proximal station reference marker 46A abuts the proximal end 50 of the outer catheter 22, the emanator 36 is aligned with a last orifice station 28E.

Figure 3A:
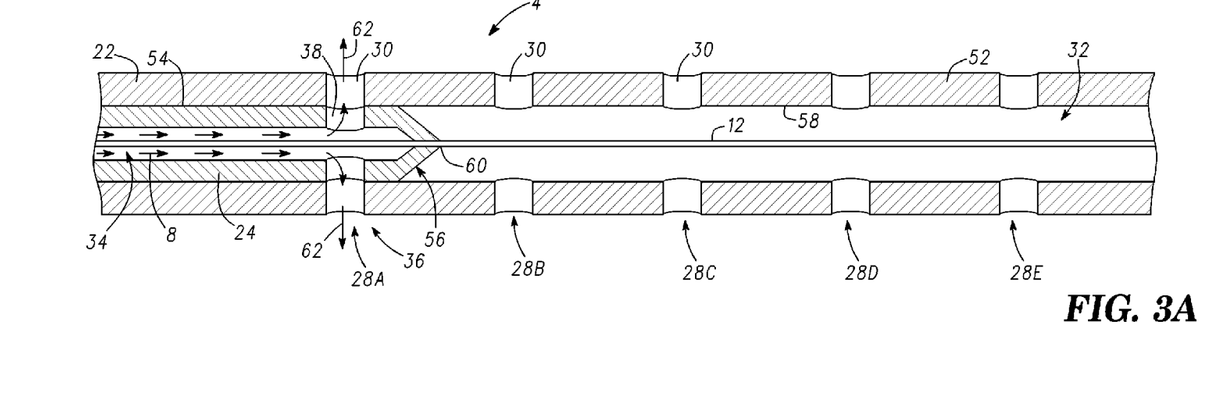
FIG. 3A illustrates a cross-section of the multi-station hydrodynamic catheter in FIG. 2 infusing at a first orifice station.

FIG. 3A illustrates a cross-section of the multi-station hydrodynamic catheter 4 in FIG. 2. As illustrated in FIG. 3A, the outer catheter 22 includes the plurality of orifice stations 28 positioned along the portion of the outer catheter 22. Each orifice station 28 includes one or more orifices 30 extending from an outer catheter external surface 52 to the first lumen 32. The inner catheter 24 is positioned within the first lumen 32 of the outer catheter 22. The inner catheter 24 includes the at least one emanator 36 including one or more fluid delivery ports 38 extending from an inner catheter external surface 54 to the second lumen 34. The inner catheter 24 is moveable within the first lumen 32 and has a diameter such that the inner catheter external surface 54 is adjacent to or in surface-to-surface contact with an outer catheter internal surface 58.

FIG. 3A further shows the guidewire 12 extending through the second lumen 34 of the inner catheter 24. The guidewire 12 facilitates navigation through the vasculature and further allows for sliding movement of the components of the multi-station hydrodynamic catheter 4. In an example, a distal end 56 of the inner catheter 24 is tapered and contacts the guidewire 12 to form a dynamic seal 60 between the guidewire 12 and the inner catheter 24. The dynamic seal 60 substantially closes the second lumen 34 such that the fluid 8 is substantially directed out of the fluid delivery ports 38 of the emanator 36.

As illustrated in FIG. 3A, the inner catheter 24 is positioned at a first orifice station 28A. At the first orifice station 28A, the one or more fluid delivery ports 38 of the emanator 36 are in fluid communication with the one or more orifices 30 of the first orifice station 28A of the plurality of orifice stations 28. The fluid 8 travels along the second lumen 34, through the fluid delivery ports 38, and through the one or more orifices 30 of the first orifice station 28A to deliver a first fluid jet 62 (or jets with a plurality of orifices 30) to a vessel for hydrodynamic engagement with the thrombus.

Figure 3B:
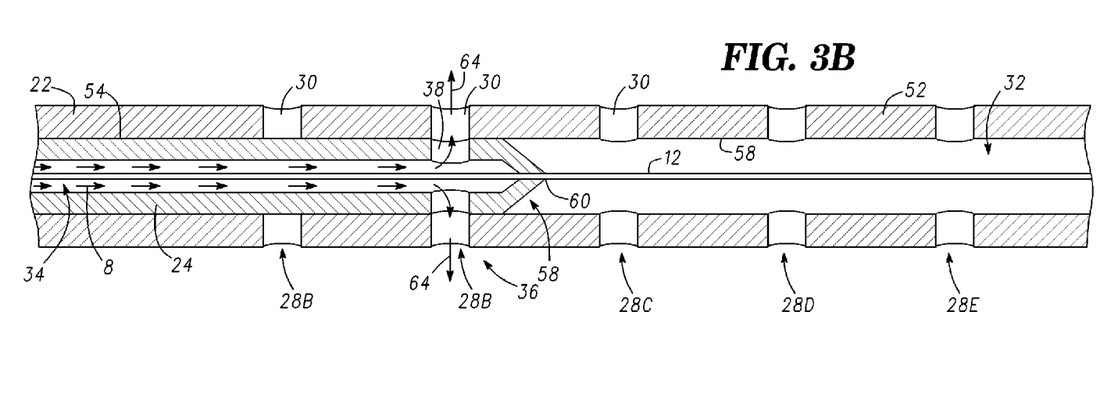
FIG. 3B illustrates a cross-section of the multi-station hydrodynamic catheter in FIG. 2 infusing at a second orifice station.

FIG. 3B illustrates a cross-section of the multi-station hydrodynamic catheter 4 previously shown in FIG. 2. As illustrated in FIG. 3B, the inner catheter 24 is positioned at a second orifice station 28B of the plurality of orifice stations 28. The second orifice station 28B is positioned distal relative to the first orifice station 28A. At the second orifice station 28B, the one or more fluid delivery ports 38 of the emanator 36 are in fluid communication with the one or more orifices 30 of the second orifice station 28B. The fluid 8 travels along the second lumen 34, through the fluid delivery ports 38, and through the one or more orifices 30 of the second orifice station 28B to deliver a second fluid jet 64 (or jets with a plurality of orifices 30) to the vessel for hydrodynamic engagement with thrombus. The multiple orifice stations 28 of the outer catheter 22 when used in cooperation with the movable inner catheter 24 provide a plurality of fluid jets 62, 64 at varying longitudinal locations along the outer catheter 22. Accordingly, with the outer catheter 22 resting within a thrombus deposit, the inner catheter 24 can move within the lumen 32 longitudinally to provide the fluid jets at varying locations within the thrombus without requiring further navigation or reorientation of the outer catheter 22.

Figure 4:
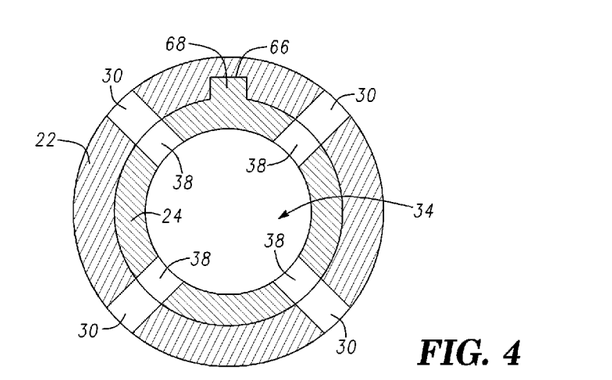
FIG. 4 illustrates a cross-section of a multi-station hydrodynamic catheter, in accordance with one embodiment of the present disclosure.

FIG. 4 illustrates a cross-section of a multi-station hydrodynamic catheter, in accordance with one embodiment of the present disclosure. As illustrated in FIG. 4, the inner catheter 24 is positioned within the outer catheter 22. In an example, the outer catheter 22 includes a groove 66 and the inner catheter 24 includes a projection 68. The groove 66 extends along a length of the outer catheter 22 and the projection 68 extends along at least a portion of the inner catheter 24. The groove 66 is optionally formed between two adjacent orifices 30 and the projection is optionally formed between two adjacent fluid delivery ports 38. The groove 66 receives the projection 68 and retains the inner catheter 24 in a substantially aligned configuration with the outer catheter 22. The aligned configuration provided by the groove 66 in combination with the projection 68 prevents rotation of the inner catheter 24 relative to the outer catheter 22. Further, the cooperation of the groove 66 and the projection 68 ensures the fluid delivery ports 38 are reliably aligned with corresponding orifices 30 at each of the orifice stations 28 even with repeated reciprocation of the inner catheter 24 within the outer catheter 22. In another example, the outer catheter 22 includes the projection and the inner catheter 24 includes the groove.

Figure 5:
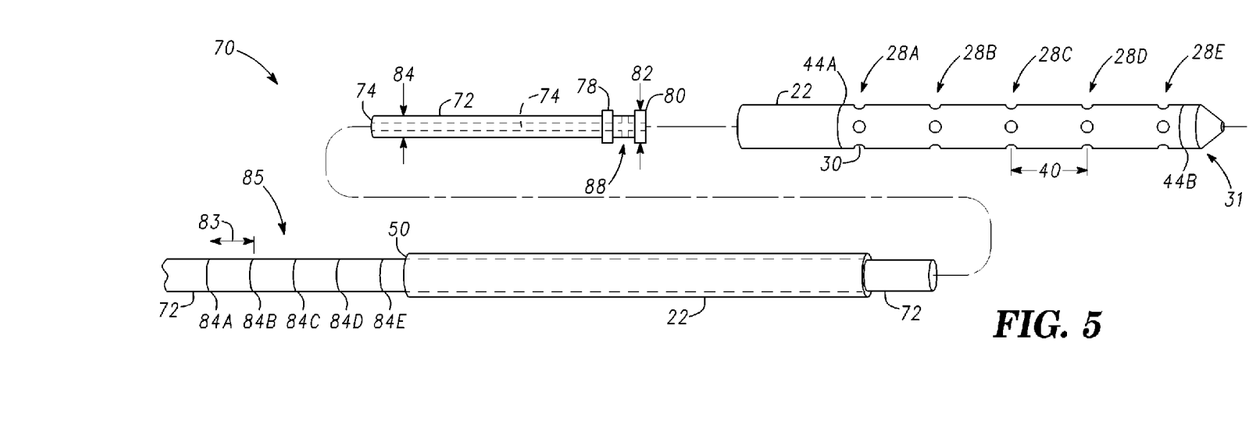
FIG. 5 illustrates an exploded view of a multi-station hydrodynamic catheter, in accordance with one embodiment of the present disclosure.

FIG. 5 illustrates an exploded view of another example of a multi-station hydrodynamic catheter, multi-station hydrodynamic catheter 70, in accordance with one embodiment of the present disclosure. The multi-station hydrodynamic catheter 70 includes the outer catheter 22 as described herein with reference to FIGS. 1-4 and an inner catheter 72. As discussed herein, the outer catheter 22 includes the plurality of orifice stations 28 each including one or more orifices 30 positioned along a portion of the outer catheter 22. Each orifice station 28 is spaced from an adjacent orifice station 28 by a distance 40. Optionally, the distance 40 varies between each of the stations. In a similar manner to the outer catheter 22 previously described above, the outer catheter 22 includes radiopaque markers 44A-B that are positioned on each side of the plurality of orifice stations 28 facilitating the positioning of the plurality of orifice stations 28 along a portion of the vessel including the thrombus.

The inner catheter 72 shown in FIG. 5 includes a second lumen 74 and a fluid reservoir 76 (e.g., an exterior fluid reservoir positioned along an exterior of the inner catheter 72 and correspondingly along the interior of the outer catheter 22) positioned toward a distal portion 88 of the inner catheter 72. The fluid reservoir 76 (hereinafter referred to interchangeably as "exterior fluid reservoir 76") is in fluid communication with the second lumen 74. In an example, a proximal sealing shoulder 78 and a distal sealing shoulder 80 form the fluid reservoir 76. The inner catheter 72 is moveable within the first lumen 32 of the outer catheter 22 such that, at multiple positions within the outer catheter 22, the fluid reservoir 76 aligns with each one of the plurality of orifice stations 28. When the fluid reservoir 76 is aligned with a first orifice station 28A of the plurality of orifice stations 28, the fluid reservoir 76 is in fluid communication with the one or more orifices 30 of the first orifice station 28A. As shown in FIG. 5, the second lumen 74 is configured to deliver the pressurized fluid to the fluid reservoir 76 and, by way of the reservoir, to the one or more respective orifices 30 of the first orifice station 28A used in a thrombectomy procedure. As discussed herein, the one or more orifices 30 of the plurality of orifice stations 28 provide corresponding fluid jets at pressures discussed herein within the lumen 74 for hydrodynamic engagement and removal of thrombus.

Optionally, the inner catheter 72 includes a plurality of station reference markers 84A-E (collectively referred to as "station reference markers 84") positioned along a proximal portion 85 of the inner catheter 72. In the example shown, the number of the station reference markers 84 equals the number of orifice stations 28 positioned along the outer catheter 22. The station reference markers 84 are spaced apart a distance 83 that is substantially the same as the distance 40 between each of the corresponding orifice stations 28. The station reference markers 84 aide an operator when advancing the inner catheter 72 to the first orifice station, and from the first orifice station (e.g., orifice station 28A) to a second orifice station (e.g., orifice station 28B). In a similar manner, the station reference markers 84 assist the operator in accurately positioning the fluid reservoir 76 (e.g., an exterior fluid reservoir positioned along an exterior of the inner catheter 72 and correspondingly along the interior of the outer catheter 22) at any of the orifice stations 28. In an example, when the most-distal station reference marker 84E abuts a reference portion 50 of the outer catheter 22, the fluid reservoir 76 is aligned with a first orifice station 28A. That is, the fluid reservoir 76 is in fluid communication with the one or more orifices 30 of the first orifice station 28A. When the most-proximal station reference marker 84A abuts the reference end 50 of the outer catheter 22, the fluid reservoir 76 is aligned with a most-distal orifice station 28E. That is, the fluid reservoir 76 is in fluid communication with the one or more orifices 30 of the orifice station 28E. The operator is accordingly able to translate (e.g., "walk") the inner catheter 72 within the outer catheter 22 and accurately position the fluid reservoir 76 at each of the orifice stations 28 without imaging techniques (e.g., fluoroscopy and the like). Instead, by aligning the respective reference marks 84 with a corresponding marker, such as the proximal end of the outer catheter 22, the operator is reliably able to position the reservoir 76 at a plurality of stations 28 and accordingly treat elongate thrombus deposits.

As illustrated in FIG. 5 a diameter 82 of the proximal sealing shoulder 78 and the distal sealing shoulder 80 is greater than a diameter 84 of a cross-section along a portion of the inner catheter 72 proximal to the proximal sealing shoulder 78. In an example, the diameter 82 of the proximal and distal sealing shoulders 78, 80 have substantially equal diameters. The sealing shoulders 78, 80 accordingly close the fluid reservoir and facilitate the movement of the reservoir within the outer catheter 22 while at the same time maintaining the fluid contents of the reservoir therein during movement. Further, the remainder of the inner catheter 72 has a smaller diameter 84 than the diameter 84 of the sealing shoulders 78, 80. Accordingly the inner catheter 72 engages in surface to surface contact with the outer catheter 22 at the sealing shoulders 78, 80, and is otherwise free to move within the outer catheter 22. The inner catheter 72, in one example, is thereby able to freely translate without friction between a substantial portion of the inner and outer catheters 72, 22.

Figure 6A:
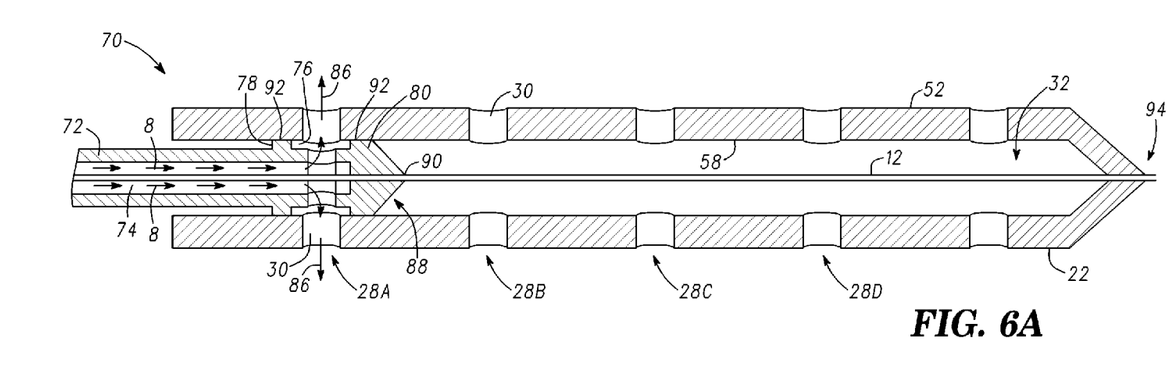
FIG. 6A illustrates a cross-section of the multi-station hydrodynamic catheter in FIG. 5 infusing at a first orifice station.

FIG. 6A illustrates a cross-section of the multi-station hydrodynamic catheter 70 in FIG. 5. As illustrated in FIG. 6A, the outer catheter 22 includes the plurality of orifice stations 28 positioned along a portion of the outer catheter 22. Each orifice station 28 includes one or more orifices 30 extending from an outer catheter external surface 52 to the first lumen 32. The inner catheter 72 is positioned within the first lumen 32 of the outer catheter 22. The inner catheter 72 includes the exterior fluid reservoir 76 in fluid communication with the second lumen 74. The inner catheter 72 is moveable within the lumen 32 of the outer catheter 22. As illustrated in FIG. 6A, the proximal and distal sealing shoulders 78, 80 engage (e.g., are in surface to surface contact) with an outer catheter internal surface 58 forming a dynamic seal 92 between the inner catheter 72 and the outer catheter 22. The dynamic seal 92 closes the exterior fluid reservoir 76 and assists in directing the fluid 8 through the fluid reservoir 76 toward the one or more orifices 30 of the first orifice station 28A.

FIG. 6A further shows the guidewire 12 extending through the second lumen 74 of the inner catheter 72. The guidewire 12 facilitates navigation through the vasculature and further allows for sliding movement of the components of the multi-station hydrodynamic catheter 70. In an example, a distal end 88 of the inner catheter 72 is tapered and contacts the guidewire 12 forming a second dynamic seal 90 between the guidewire 12 and the inner catheter 72. The second dynamic seal 90 substantially closes the second lumen 72 and assists in directing the fluid 8 through the fluid reservoir 76 toward the one or more orifices 30 of the first orifice station 28A. In an example, a distal end 94 of the outer catheter 22 is tapered and contacts the guidewire 12 to form a third dynamic seal 96 between the guidewire 12 and the outer catheter 22. The dynamic seals 90, 92, 96 assist in guiding the flow of fluid within the multi-station hydrodynamic catheter 70 to the orifices 30 of each of the orifice stations 28. That is to say, the seals 90, 92, 96 cooperate with the fluid reservoir 76 to ensure that fluid is reliably delivered to the orifice stations 28.

As illustrated in FIG. 6A, the inner catheter 72 is positioned at a first orifice station 28A. At the first orifice station 28A, the fluid reservoir 76 is in fluid communication with the one or more orifices 30 of the first orifice station 28A. The fluid 8 travels along the lumen 74, through the fluid reservoir 76, and by way of the reservoir 76 through the one or more orifices 30 of the first orifice station 28A to deliver one or more first fluid jets 86 to the vessel for hydrodynamic engagement and removal of thrombus.

Figure 6B:
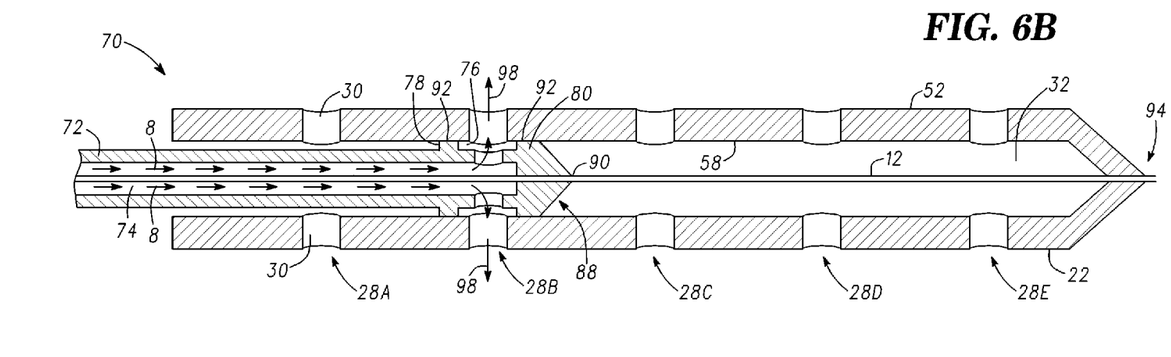
FIG. 6B illustrates a cross-section of the multi-station hydrodynamic catheter in FIG. 5 infusing at a second orifice station.

FIG. 6B illustrates a cross-section of the multi-station hydrodynamic catheter 70 previously shown in FIG. 5. As illustrated in FIG. 6B, the inner catheter 72 is translated distally and the fluid reservoir 76 is positioned at a second orifice station 28B of the plurality of orifice stations 28. As shown, the second orifice station 28B is positioned distally relative to the first orifice station 28A. At the second orifice station 28B, the exterior fluid reservoir 76 is in fluid communication with the one or more orifices 30 of the second orifice station 28B. The infusion fluid 8 is delivered along the second lumen 34, through the fluid reservoir 76, and through the one or more orifices 30 of the second orifice station 28B (by way of the reservoir 76) to deliver a second fluid jet 98 to the vessel for hydrodynamic engagement with thrombus. In the exemplary multi-station hydrodynamic catheter 70 shown in FIGS. 5, 6A, B the inner catheter 72 includes an fluid reservoir movable within the outer catheter 22 between each of the orifice stations 28. Alignment of the reservoir 76 with each of the orifices 30 at the stations 28 is provided axially (e.g., with the reference marks 84). Radial alignment of the orifices 30 is not needed because (in at least one example) the reservoir 76 forms a ring of infusion fluid around the inner catheter 72 in communication with each of the orifices 30 at each station 28.

Figure 7:
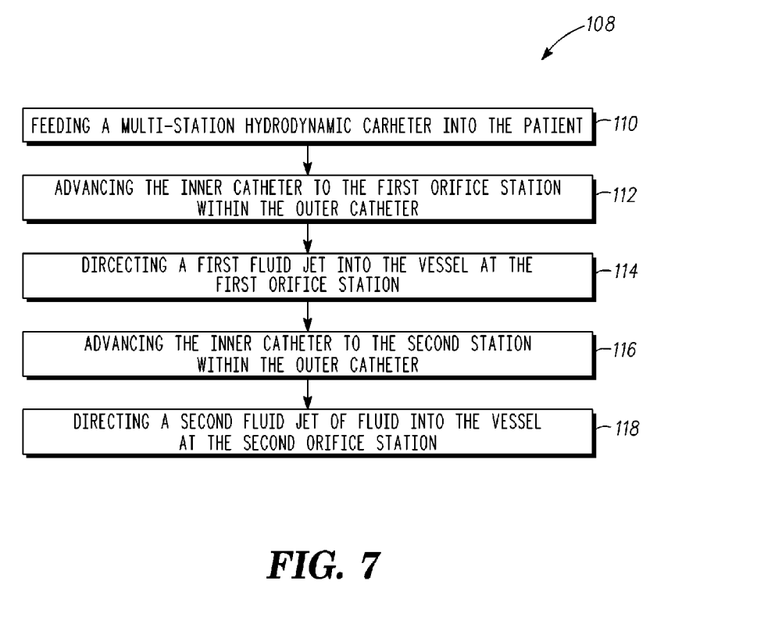
FIG. 7 is a flow chart showing a method, in accordance with one embodiment of the present disclosure.

FIG. 7 is a flow chart of a method 108, in accordance with one embodiment of the present disclosure. At 110, a multi-station hydrodynamic catheter is fed into a patient. For example, either of the multi-station hydrodynamic catheter 4, shown in FIGS. 1-4 or the multi-station hydrodynamic catheter 70, shown in FIGS. 5-6, is used in the method 108. In an example, the multi-station hydrodynamic catheter 4 includes an outer catheter 22 having a first lumen 32. The outer catheter 22 has a plurality of orifice stations 28A-E positioned along a portion of the outer catheter 22. Each orifice station 28 includes one or more orifices 30 extending from an outer catheter external surface 52 to the first lumen 32. The multi-station hydrodynamic catheter 4 also includes an inner catheter 24 having a second lumen 34, and the inner catheter 24 is movable within the first lumen 32 between each of the orifice stations of the plurality of orifice stations 28 (e.g., at least first and second orifice stations 28A, B).

At 112, the inner catheter 24 (72) is advanced to a first orifice station within the outer catheter. For example, inner catheter 24 is advanced to the first orifice station 28A within the outer catheter 22 as shown in FIG. 3A. At the first orifice station 28A, the fluid delivery ports 38 are in fluid communication with the orifices 30 of the first orifice station 28A. In an example advancing the inner catheter 24 (of the multi-station hydrodynamic catheter 4) to the first orifice station 28A includes positioning one or more fluid delivery ports 38 of an emanator 36 of the inner catheter 24 in fluid communication with the one or more orifices 30 of the first orifice station 28A. In another example, advancing the inner catheter 72 of the multi-station hydrodynamic catheter 70 shown in FIGS. 5, 6A, B) to the first orifice station 28A includes positioning the fluid reservoir 76 of the inner catheter 72 in fluid communication with the one or more orifices 30 of the first orifice station 28A.

At 114, a first fluid jet is directed into the vessel at the first orifice station. In an example, the first fluid jet 62, as shown in FIG. 3A with the multi-station hydrodynamic catheter 4, or the first fluid jet 86, as shown in FIG. 6A with the multi-station hydrodynamic catheter 70, is directed into the vessel at the first fluid orifice station 28A. For instance, the first fluid orifice station 28A corresponds to a first location of interest (e.g., corresponding to a location of thrombus within the vessel).

At 116, the inner catheter is advanced to a second orifice station 28B within the outer catheter 22. For example, the inner catheter 24 is advanced to the second orifice station 28B within the outer catheter 22, as shown in FIG. 3B. At the second orifice station 28B, the fluid delivery ports 38 are in fluid communication with the orifices 30 of the second orifice station 28B. As described herein, one or more projections received within one or more corresponding grooves align the orifices 30 with the fluid delivery ports 38 and accordingly ensure delivery of the infusion fluid at each of the orifice stations 28. In an example, with the multi-station hydrodynamic catheter 70, at the second orifice station 28B, the fluid reservoir 76 provides a pool or ring of fluid around the exterior of the inner catheter 72 and correspondingly along the interior of the outer catheter 22. Accordingly, the fluid reservoir 76 fluidly communicates automatically with each of the orifices 30 of the second orifice station 28B, as shown in FIG. 6B.

In an example of method 108, advancing the inner catheter 24 to the second orifice station 28B within the outer catheter 22 includes operating a motor that advances the inner catheter 24 a distance within the outer catheter 22. In one example, the motor 14 shown in FIG. 1 advances the inner catheter 24 (72) relative to the outer catheter 22. Optionally, the distance the motor advances the inner catheter 24 equals a distance 40 between the first orifice station 28A and the second orifice station 28B, as shown in FIG. 2. In another example, a controller 16 coupled with the motor 14 cooperates with an encoder associated with the inner and outer catheters 22, 24 (22, 72) and advances the inner catheter 24 (72) according to reference markings, such as reference markings 84. In still another example, the controller 16 for the motor 14 is coupled with a translation sensor coupled along the inner catheter and is accordingly able to measure the translation of the inner catheter 24 (72) and arrest movement as the inner catheter 24 (72) is moved into a position corresponding to a desired orifice station 28 of the outer catheter 22.

At 118, a second fluid jet is directed into the vessel at the second orifice station. In an example, the second fluid jet 64 (as shown in FIG. 3B) or the second fluid jet 98 (as shown in FIG. 6B) is directed into the vessel at the second fluid orifice station 28B. For instance, the second fluid orifice station 28B corresponds to a second location of interest (e.g., corresponding to a location of thrombus within the vessel). The multiple orifice stations 28 of the outer catheter 22 when used in cooperation with the movable inner catheter 24 (72) provide a plurality of fluid jets at varying longitudinal locations along the outer catheter 22. According, with the outer catheter 22 resting within a thrombus deposit, the inner catheter 24 (72) can move within the lumen 32 to provide the fluid jets at varying locations within the thrombus without requiring further navigation or reorientation of the outer catheter 22.

In an example of the method 108, directing includes pumping a volume of fluid into the vessel over a time period. For example, a volume of the fluid (e.g., a predetermined volume) is delivered to the vessel at each orifice station 28 of the plurality of orifice stations 28. In an example, the one or more orifices 30 of each of the plurality of orifice stations 30 provide a volume of fluid, including but not limited to, about 0.5 cubic centimeters (cc) to about 5 cc. In another example, the controller 16 is configured to supply a predetermined volume of infusion fluid (e.g., lytics) at each of the orifice stations 28 for a predetermined time. Optionally, the controller 16 is programmed to translate the inner catheter 24 (72) relative to the outer catheter 22 and accordingly infuse at one or more of the orifice stations 28. The operator is able, through the controller 16, to program desired infusion volumes, rates, the order of infusion (e.g., the order of the orifice station 28 infusions). The controller 16 operates each of the infusion delivery pump 10 and the motor 14 to accordingly translate and infuse at each of the orifice stations 28 according to the programmed scenario.

In an example, the volume of the fluid delivered to the vessel at each orifice stations 28 is delivered in a single fluid jet. In another example, the volume of the fluid delivered to the vessel at each orifice station 28 is delivered as a pulsed fluid jet (e.g., in a plurality of pulsed fluid jets in sequence over a time period. In that instance, each pulse is spaced apart by a time interval within a specified time period. In an example, 2 cc is delivered to a vessel in pulsed fluid jets, where the fluid jets are spaced apart by 20 minutes.

In an example, flow rates including but not limited to about 1 m/s to about 30 m/s are used to provide the fluid jets to the vessel through the one or more orifices 30 of the plurality of orifice stations 28. In another example, the fluid jets are provided to the vessel having flow rates, including but not limited to about 10 m/s to 20 m/s. In still another example, the fluid jets are provided to the vessel having flow rates, including but not limited to about 15 cc/s. The velocity of and flow rate of the fluid jets delivered from the one or more orifices 30 of the plurality of orifice stations 28 is dependent on the flow rate and pressure of the fluid source, the size and shape of the fluid delivery ports 28, the size and shape of the fluid reservoir 76, and the one or more orifices 30 of each orifice station 28. The multi-station hydrodynamic catheters 4, 70, described herein, provide a catheter system configured to provide a pressurized fluid (e.g., fluid jets) at multiple orifice stations 28 for removal of a thrombus from a vessel. By providing the direct pressurized fluid delivery along the multiple orifice stations 28, the fluid jets penetrate the blood clot more effectively and reduce the procedure time as compared to other methods. That is to say, the fluid jets at each of the orifice stations 28 localize the delivery of fluid, such as, lytics at locations along a vessel (for instance at longitudinally varied locations of a thrombus deposit). In effect, the inner catheter 24, 72 is translated from orifice station to orifice station 28 and accordingly provides localized acute treatment to the thrombus at each of the corresponding stations 28.

In an example, prior to feeding a multi-station hydrodynamic catheter into the patient, the method 108 includes feeding a guidewire into the patient to a position within a vessel, such as the guidewire 12 in FIGS. 3A and 3B. In an example, the method 108 includes removing, prior to directing the first fluid jet, the guidewire, such as guidewire 12 in FIGS. 3A and 3B. For instance, with the removal of the guidewire 12 enhanced fluid flow is realized as the lumen 34 (74) of the inner catheter 24 (72) is vacant and accordingly able to deliver additional infusion fluid.

Figure 8:
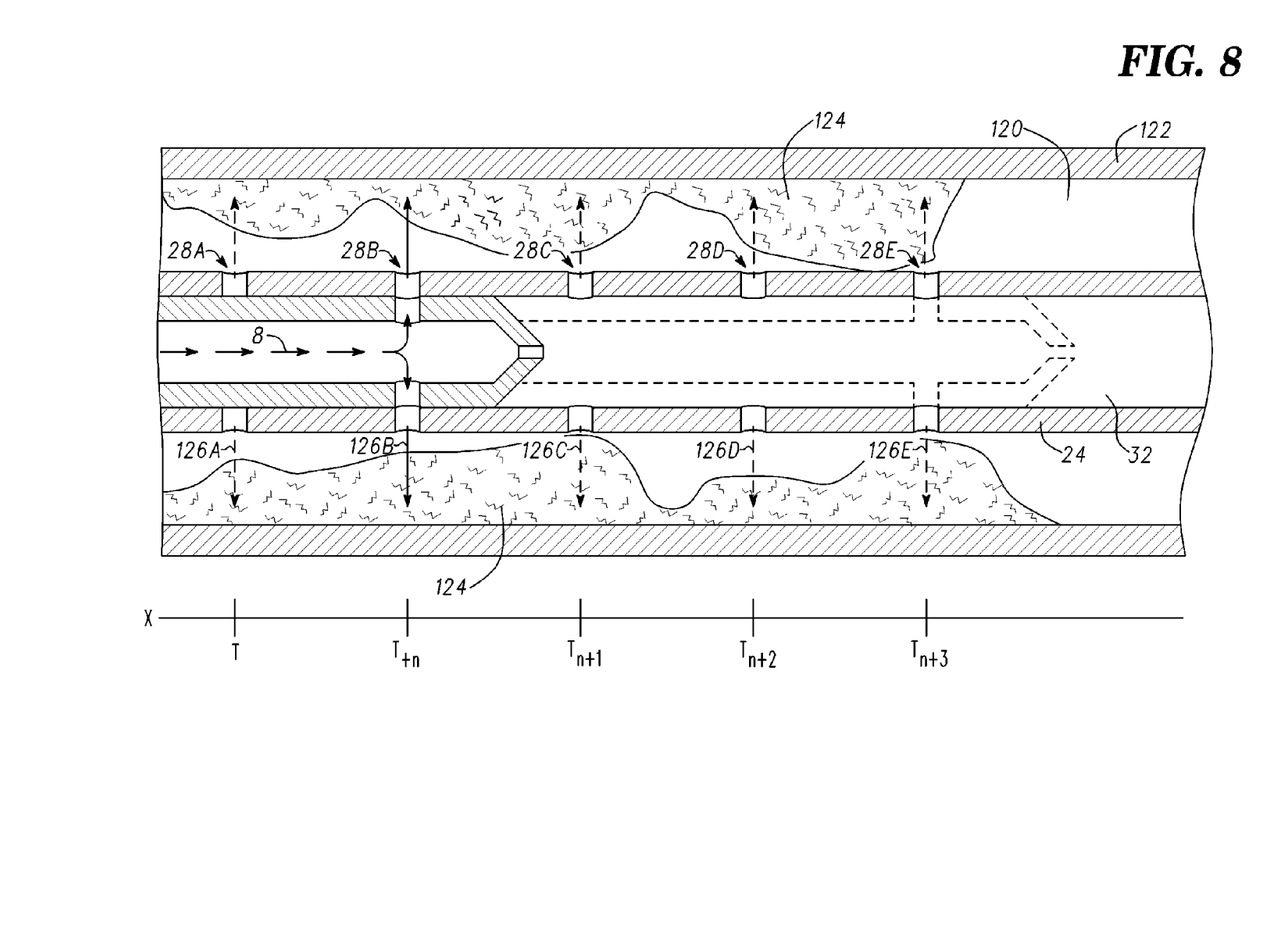
FIG. 8 illustrates the method, in accordance with one embodiment of the present disclosure.

FIG. 8 illustrates the method 108, in accordance with one embodiment of the present disclosure. The method 108 as illustrated in FIG. 8 uses the multi-station hydrodynamic catheter 4, as shown in FIGS. 1-4 for treating a blood clot (e.g., thrombus 124) along multiple stations (e.g., the plurality of orifice stations 28). In other words, the thrombus 124 is treated in multiple steps along the length of the thrombus 124, where at each step (e.g., an orifice station 28) a fluid jet is delivered into the vessel to locally treat (and optionally remove or penetrate) the thrombus 124.

As illustrated in FIG. 8, the multi-station hydrodynamic catheter 4 is positioned within a lumen 120 of a vessel 120 including the thrombus 124. The multi-station hydrodynamic catheter 4 includes the internal catheter 24 positioned within the lumen 32 of the outer catheter 22. For simplicity, the guidewire 12 is not shown in FIG. 8. However, as discussed herein, the guidewire 12 may or may not be present during the thrombectomy treatment. The multi-station hydrodynamic catheter 4 delivers a plurality of fluid jets 126A-E (collectively referred to as "fluid jets 126") to the thrombus deposit 124. As described above, the inner catheter 24 is advanced ("walked") to each of the orifice stations 28 within the thrombus to provide directed localized treatment to the thrombus deposit at each location. By providing the localized delivery at multiple orifice stations 28, the fluid 8 more effectively treats the entire deposit (e.g., penetrates, locally delivers treatment such as lytics, removes thrombus through hydrodynamic engagement or the like) and reduces the procedure time as compared to other methods. For instance, the operator is able to leave the outer catheter 22 at a static location and gradually move the inner catheter 24 (72) as needed to each of the stations 28 without otherwise disturbing the outer catheter and treatment region. Additionally, the operator may leave the outer catheter 22 in place after a procedure, and another technician (physician, nurse and the like) may advance or retract the inner catheter 24 (72) as needed to treat the thrombus deposit 124.

As shown in FIG. 8, the multi-station hydrodynamic catheter 4 has delivered a first fluid jet 126A of the fluid 8 to the vessel 122 (including the thrombus 124) at the first orifice station 28A at time (T). As discussed herein, a volume of the fluid 8 is delivered to the vessel 122 at the first orifice station 28A by either a single fluid jet 126A or a plurality of fluid jets 126A (e.g., timed pulses of fluid 8). Once the volume of the fluid 8 is delivered to the vessel at the first orifice station 28A, the multi-station hydrodynamic catheter 4 is advanced to a second orifice station 28B. At the second orifice station 28B, a second fluid jet 126B of the fluid 8 is directed to the vessel 122 at the second orifice station 28B at time ($T_n$), where "n" is a time interval after the first fluid jet 126A has been delivered to the vessel 122. As illustrated in FIG. 8, the multi-station hydrodynamic catheter 4 is advanced to the most-distal orifice station 28E, where a last fluid jet 126E is delivered to the vessel 122 at time ($T_{n+3}$).

As discussed herein, the direct pressurized delivery of the fluid along multiple orifice stations 28A-E penetrates the thrombus 124 more effectively (accordingly removing thrombus effectively) and reduces the procedure time as compared to other methods. Since the fluid 8 engages directly with the entirety of the thrombus and at high pressure (according to the use of the orifice stations 28) the amount of time for the fluid 8 to interact with the thrombus 124 (hydrodynamically or chemically) is reduced, thereby enhancing the efficiency of the thrombectomy technique. Thus, the present subject matter reduces the procedure times and enhances the effectiveness of thrombectomy with thrombus deposits that benefit from multi-station treatment.

VARIOUS NOTES & EXAMPLES

Each of these non-limiting examples can stand on its own, or can be combined in any permutation or combination with any one or more of the other example.

Example 1 can include subject matter such as a catheter system. The catheter system includes a multi-station hydrodynamic catheter. The multi-station hydrodynamic catheter includes an outer catheter having a first lumen, the outer catheter having a plurality of orifice stations positioned along a portion of the outer catheter, wherein each orifice station includes one or more orifices extending from an outer catheter external surface to the first lumen. The multi-station hydrodynamic catheter also includes an inner catheter having a second lumen, the inner catheter movable within the first lumen and includes at least one emanator, wherein the at least one emanator includes one or more fluid delivery ports extending from an inner catheter external surface to the second lumen, the inner catheter movable within the first lumen between a first orifice station and a second orifice station of the plurality of orifice stations. At the first orifice station, the one or more fluid delivery ports of the emanator are in fluid communication with the one or more orifices of the first orifice station of the plurality of orifice stations. At the second orifice station, the one or more fluid delivery ports of the emanator are in fluid communication with the one or more orifices of a second orifice station of the plurality of orifice stations. The second orifice station is positioned distally relative to the first orifice station. The one or more orifices at the first orifice station are configured to generate a first fluid jet and the one or more orifices at the second orifice station are configured to generate a second fluid jet distal to the first fluid jet.

Example 2 can include, or can optionally be combined with the subject matter of Example 1, to optionally include where the plurality of orifice stations are symmetrically spaced along a longitudinal axis of the outer catheter.

Example 3 can include, or can optionally be combined with the subject matter of Example 1 or 2, to optionally include where the orifices of each of the plurality of orifice stations are radially spaced along a periphery of the outer catheter.

Example 4 can include, or can optionally be combined with the subject matter of one or any combination of Examples 1 through 3 to optionally include a guidewire positioned within the second lumen, wherein a dynamic seal is formed between the guidewire and a distal end of the inner catheter, the dynamic seal closing the second lumen.

Example 5 can include, or can optionally be combined with the subject matter of one or any combination of Examples 1 through 4, to optionally include where the distal end of the inner catheter is tapered and configured to contact the guidewire to form the dynamic seal.

Example 6 can include, or can optionally be combined with the subject matter of Examples 1 through 5 to optionally include where the outer catheter and the inner catheter are slidably coupled to each other.

Example 7 can include, or can optionally be combined with the subject matter of Examples 1 through 6 to optionally include where the outer catheter includes an internal surface having a substantially straight groove extending from a distal end to a proximal end, and the inner catheter includes an external surface having a projection extending from a distal end to a proximal end, the projection configured to move along the substantially straight groove.

Example 8 can include, or can optionally be combined with the subject matter of Examples 1 through 7 to optionally include where the distal end of the inner catheter includes one or more station reference marks, wherein the one or more station reference marks correspond to a respective orifice station of the plurality of orifice stations.

Example 9 can include, or can optionally be combined with the subject matter of Examples 1 through 8 to optionally include a pressurized source of fluid configured to generate the first and second fluid jet, the pressurized source of fluid in fluid communication with the second lumen.

Example 10 can include, or can optionally be combined with the subject matter of Examples 1 through 9 to optionally include a fluid reservoir configured to contain the fluid, a pumping device configured to pump a volume of the fluid from the fluid reservoir into the second lumen to generate a pressurized source of fluid within the second lumen, a motor coupled to the distal end of the inner catheter and moves the inner catheter from the first position to the second position, and a control unit operably coupled to the pumping device and the motor, wherein the control unit operates the pumping device to selectively pump the fluid, and wherein the control unit operates the motor to selectively move the inner catheter from the first orifice station to the second orifice station.

Example 11 can include subject matter such as a catheter system. The catheter system includes a multi-station hydrodynamic catheter. The multi-station hydrodynamic catheter includes an outer catheter having a first lumen, the outer catheter having a plurality of orifice stations positioned along a portion of the outer catheter, where each orifice station includes one or more orifices extending from an outer catheter external surface to the first lumen. The multi-station hydrodynamic catheter includes an inner catheter having a second lumen, the inner catheter movable within the first lumen and includes a fluid reservoir, the fluid reservoir in fluid communication with the second lumen. The inner catheter movable within the first lumen, between first and second orifice stations of the plurality of orifice stations, where at the first orifice station, the fluid reservoir is in fluid communication with the one or more orifices of the first orifice station. At the second orifice station, the fluid reservoir is in fluid communication with the one or more orifices of the second orifice station, the second orifice station distal to the first orifice station. The fluid reservoir at the first orifice station generates a first fluid jet through the one or more orifices when supplied with a pressurized fluid, and the fluid reservoir at the second orifice station generates a second fluid jet through the one or more orifices when supplied with a pressurized fluid distal to the first fluid jet.

Example 12 can include, or can optionally be combined with the subject matter of Examples 1 through 11 to optionally include where the inner catheter includes a proximal sealing shoulder and a distal sealing shoulder that define the fluid reservoir.

Example 13 can include, or can optionally be combined with the subject matter of Examples 1 through 12 to optionally include where the proximal sealing shoulder and the distal sealing shoulder contact an outer catheter inner surface and form a dynamic seal between the inner catheter and the outer catheter, the dynamic seal closing the fluid reservoir.

Example 14 can include, or can optionally be combined with the subject matter of Examples 1 through 13 to optionally include where a first diameter of a cross-section of the proximal sealing shoulder and the distal sealing shoulder is greater than a second diameter of a cross-section along a portion of the inner catheter positioned proximal to the proximal sealing shoulder.

Example 15 can include, or can optionally be combined with the subject matter of Examples 1 through 14 to optionally include a guidewire positioned within the second lumen and extending through a distal end of the outer catheter, wherein a dynamic seal is formed between the distal sealing shoulder and the guidewire, the dynamic deal closing the first lumen.

Example 16 can include, or can optionally be combined with the subject matter of Examples 1 through 15 to optionally include where the distal end of the outer catheter is tapered and configured to contact the guidewire to form a dynamic seal.

Example 17 can include, or can optionally be combined with the subject matter of Examples 1 through 16 to optionally include a pressurized source of fluid configured to generate the first and second fluid jet, the pressurized source of fluid in fluid communication with the fluid reservoir.

Example 18 can include, or can optionally be combined with the subject matter of Examples 1 through 17 to optionally include a fluid reservoir containing the fluid, a pump that delivers a volume of the fluid from the fluid reservoir into the fluid reservoir to generate a pressurized source of fluid, and a motor coupled to the distal end of the inner catheter and moves the inner catheter from the first position to the second position, and a control unit operably coupled to the pump and the motor, wherein the control unit operates the pump to selectively pump the fluid, and wherein the control unit operates the motor to selectively move the inner catheter from the first orifice station to the second orifice station.

Example 19 can include subject matter such as a method. The method can include feeding a multi-station hydrodynamic catheter into the patient. The multi-station hydrodynamic catheter includes an outer catheter having a first lumen, the outer catheter having a plurality of orifice stations positioned along a portion of the outer catheter, where each orifice station includes one or more orifices extending from an outer catheter external surface to the first lumen. The multi-station hydrodynamic catheter also includes an inner catheter having a second lumen, the inner catheter movable within the first lumen between a first orifice station and a second orifice station of the plurality of orifice stations. The method includes advancing the inner catheter to the first orifice station within the outer catheter, where at the first orifice station, the second lumen is in fluid communication with the one or more orifices of the first orifice station of the plurality of orifice stations and directing a first fluid jet into the vessel at the first orifice station. The method also includes advancing the inner catheter to the second orifice station within the outer catheter, where at the second orifice station, the second lumen is in fluid communication with the one or more orifices of the second orifice station of the plurality of orifice stations, the second orifice station distal to the first orifice station, and directing a second fluid jet of fluid into the vessel at the second orifice station.

Example 20 can include, or can optionally be combined with the subject matter of Examples 1 through 19 to optionally include where directing includes pumping a volume of fluid into the vessel over a time period.

Example 21 can include, or can optionally be combined with the subject matter of Examples 1 through 20 to optionally include where the first fluid jet is a pulsed fluid jet.

Example 22 can include, or can optionally be combined with the subject matter of Examples 1 through 21 to optionally include where advancing the inner catheter to the second orifice station within the outer catheter includes operating a motor that advances the inner catheter a predetermined distance within the outer catheter, the predetermined distance equals a distance between the first orifice station and the second orifice station.

Example 23 can include, or can optionally be combined with the subject matter of Examples 1 through 22 to optionally include where advancing the inner catheter to the first position includes positioning one or more fluid delivery ports of an emanator of the inner catheter in fluid communication with the one or more orifices of the first orifice station.

Example 24 can include, or can optionally be combined with the subject matter of Examples 1 through 23 to optionally include where advancing the inner catheter to the first position includes positioning a fluid reservoir of the inner catheter in fluid communication with the one or more orifices of the first orifice station.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A catheter system comprising:
   a multi-station hydrodynamic catheter including:
      an outer catheter having a first lumen, the outer catheter having a plurality of orifice stations positioned along a portion of the outer catheter, wherein each orifice station includes one or more orifices extending from an outer catheter external surface to the first lumen; and
      an inner catheter having a second lumen, a first reference marker and a second reference marker, the inner catheter movable within the first lumen and includes at least one emanator, wherein the at least one emanator includes one or more fluid delivery ports extending from an inner catheter external surface to the second lumen,
         the inner catheter movable within the first lumen between a first orifice station and a second orifice station of the plurality of orifice stations,
         wherein at the first orifice station, the first reference marker is aligned with a reference portion of the outer catheter and the one or more fluid delivery ports of the emanator are in fluid communication with the one or more orifices of the first orifice station of the plurality of orifice stations, and at the second orifice station, the second reference marker is aligned with the reference portion of the outer catheter and the one or more fluid delivery ports of the emanator are in fluid communication with the one or more orifices of a second orifice station of the plurality of orifice stations, the second orifice station positioned distally relative to the first orifice station,
         wherein the one or more orifices at the first orifice station are configured to generate a first fluid jet and the one or more orifices at the second orifice station are configured to generate a second fluid jet distal to the first fluid jet.

2. The catheter system of claim 1, wherein the plurality of orifice stations are symmetrically spaced along a longitudinal axis of the outer catheter.

3. The catheter system of claim 1, wherein the orifices of each of the plurality of orifice stations are radially spaced along a periphery of the outer catheter.

4. The catheter system of claim 1, including
   a guidewire positioned within the second lumen, wherein a dynamic seal is formed between the guidewire and a distal end of the inner catheter, the dynamic seal closing the second lumen.

5. The catheter system of claim 4, wherein the distal end of the inner catheter is tapered and configured to contact the guidewire to form the dynamic seal.

6. The catheter system of claim 1, wherein the outer catheter and the inner catheter are slidably coupled to each other.

7. The catheter system of claim 6, wherein the outer catheter includes an internal surface having a substantially straight groove extending from a distal end to a proximal end, and the inner catheter includes an external surface having a projection extending from a distal end to a proximal end, the projection configured to move along the substantially straight groove.

8. The catheter system of claim 1, wherein the distal end of the inner catheter includes one or more station reference marks, wherein the one or more station reference marks correspond to a respective orifice station of the plurality of orifice stations.

9. The catheter system of claim 1, comprising a pressurized source of fluid configured to generate the first and second fluid jet, the pressurized source of fluid in fluid communication with the second lumen.

10. The catheter system of claim 9, comprising;
- a fluid reservoir configured to contain the fluid;
- a pumping device configured to pump a volume of the fluid from the fluid reservoir into the second lumen to generate a pressurized source of fluid within the second lumen;
- a motor coupled to the distal end of the inner catheter and moves the inner catheter from the first position to the second position; and
- a control unit operably coupled to the pumping device and the motor, wherein the control unit operates the pumping device to selectively pump the fluid, and wherein the control unit operates the motor to selectively move the inner catheter from the first orifice station to the second orifice station.

\* \* \* \* \*